United States Patent [19]

Likens, deceased et al.

[11] 4,315,916

[45] Feb. 16, 1982

[54] TOPICAL SALVE

[75] Inventors: Jonas S. Likens, deceased, late of Macon County, Tenn.; by Ruby L. Ford, heir; by Mary F. L. Coulter, heir; by Pauline L. Coulter, heir, all of Lafayette, Tenn.; by Lucille L. Filson, heir, Rte. 1, Hartsville, Tenn. 37074

[73] Assignee: Lucille L. Filson, Hartsville, Tenn.

[21] Appl. No.: 108,046

[22] Filed: Dec. 28, 1979

Related U.S. Application Data

[63] Continuation-in-part of Ser. No. 873,087, Jul. 18, 1978, Pat. No. 4,229,437.

[51] Int. Cl.³ .................... A61K 33/00; A61K 35/78
[52] U.S. Cl. .................................... 424/145; 424/195
[58] Field of Search .......................................... 424/145

[56] References Cited

U.S. PATENT DOCUMENTS

| 209,331 | 10/1878 | Daniel | 424/145 |
|---|---|---|---|
| 1,411,577 | 4/1922 | Mullins et al. | 424/145 |
| 2,344,830 | 3/1944 | Mohs | 424/145 |

OTHER PUBLICATIONS

Potter's Cyclopedia of Botanical Drugs & Prep., Published by Potter & Clark, London, 1950, p. 38.

*Primary Examiner*—Jerome D. Goldberg
*Attorney, Agent, or Firm*—Berman, Aisenberg & Platt

[57] ABSTRACT

A compound derived from dried bittersweet root bark is combined with zinc chloride to form a salve which is topically applied to remove unwanted growths from the skin.

9 Claims, 4 Drawing Figures

TOPICAL SALVE

RELATED APPLICATION

This application is a continuation-in-part of application Ser. No. 873,087, filed July 18, 1978, now U.S. Pat. No. 4,229,437. The entire disclosure of that application is incorporated herein by reference.

SUMMARY OF THE INVENTION

A composition which is a substantially uniform admixture of (a) a compound (BSO) derivable inter alia from bittersweet dried and ground root bark (BS) and (b) zinc chloride (butter of zinc) crystals (BZ) is useful for removing an external surface lesion from the skin when the composition is applied in a thin layer directly on the lesion and secured there in an air-tight fashion for a period of time while keeping the lesion and surrounding area dry and warm. BSO is an active component which, when compounded with zinc chloride, forms a medicament paste or salve useful for removing unwanted skin growths. The volume ratio of BSO to BZ is within the range of from 1:20 to 20:1.

DETAILS

Figure 1:
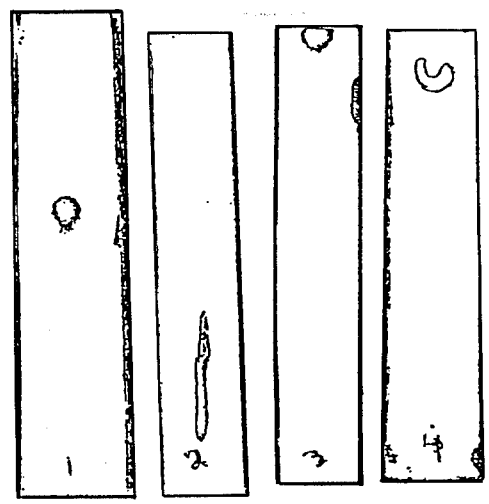
FIG. 1 shows thin layer chromatography plates on different media for BSO.

The plant referred to as bittersweet is also known as woody nightshade or *Solanum dulcamara*. The bark of the root of this plant is dried (e.g. until the bark is brittle) at a temperature from ambient temperature, e.g. about room temperature, i.e. 20° C., to about 250° F. (121° C.). When drying is effected at 250° F., drying for from about 45 to about 60 minutes (with occasional stirring) is ordinarily sufficient.

After drying the root bark until brittle, the dried bark is ground to a particle size (hereinafter referred to as powder) about the same as that of granulated sugar or even finer. The precise particle size is not critical.

Zinc chloride is a well-known compound which is available in crystalline form. Although the proportions are not exact, about one part by volume of zinc chloride crystals is conveniently compounded with three parts by volume of BS powder to formulate an exemplary composition. Compounding is effected, e.g., with a spatula on a suitable clean surface. The BS powder is mixed into the BZ to form a salve, paste or dough composition which is a substantially uniform admixture of the two components. These are the only essential ingredients; no other components are required for the composition or to achieve the desired results. The composition, however, is advantageously compounded immediately or shortly before use.

In order to determine the nature of the active component, BS powder was extracted with diethyl ether. Similar extracts were made from leaves of the same plant, from vines of the same plant and from roots of the same plant. All extracts were found to be of the same compound, which was derived in largest quantities from the dried root bark.

After evaporating the ether from the extract of the BS powder, the weight of the obtained dark oil (BSO) was found to be about ten percent of the starting BS powder. Actual testing established that the BSO was the active component. In view of the difference in concentration of the active component, far less BSO (than BS) is required to be combined with BZ to produce an effective salve or ointment. Suitable topical compositions thus have as little as about 5 percent by weight of BSO, but preferably have between 35 and 55 percent by volume of BSO. The compositions must have at least 5 percent by weight of BZ. The composition is used in the same way whether prepared with BS or BSO.

The composition is applied to an externally-visible unwanted skin growth or diseased area which is herein referred to as a lesion. This term is used to include those conditions variously known, e.g., as moles, stone moles, red moles and warts, which are removed by treatment with the composition. The existence, growth and/or spread of stone cancer (calcifying epithelioma), epithelioma adenoides cysticum or epithelioma capitis is also retarded or terminated by suitable treatment with the composition.

In order to treat a particular skin condition, a piece of clean cloth is cut to approximately the same size as the lesion. This piece of cloth is covered with the paste or dough composition (to a thickness of about that of a dime) to form a plaster with which the lesion is covered. The composition is placed directly on the lesion, and the plaster is secured in place with, e.g., adhesive tape in an air-tight manner. For twenty-four hours thereafter (for a lesion the size of a pea or smaller) the area of the lesion is kept dry and warm. Body temperature is more than adequate; the lesion area should not be permitted to contact anything having a temperature below about 15° C. (60° F.) during the specified period. (Larger lesions will require at least forty-eight hours or even longer.)

Pain is experienced for eleven or twelve hours, and it is accomplished by redness and swelling of the involved area. At the end of the twenty-four-hour (or longer) period, the plaster is removed. The entire area is thereafter bathed twice or three times daily with luke-warm water and mild soap and then dried. Between washings the lesion and surrounding area are covered with petroleum jelly or other suitable ointment or emollient, over which a thin cloth is maintained, preferably without any tape. This is continued (usually for about seven days) until the lesion is removed.

At the end of the initial application of the composition, the plaster is raised and the lesion is examined. If the treated area looks white around the edges and the lesion appears to be breaking loose, the composition has been applied for a sufficient period; otherwise, apply another similar plaster for a further twenty-four hours and maintain it under the same conditions during this period. During treatment with the composition the center of the lesion may turn black.

The following examples are merely illustrative and in no way limitative of the subject invention. In the examples all parts are by volume and all temperatures are in degrees Celsius unless otherwise stated.

EXAMPLE 1

Heat an oven to a temperature of 121° and place therein the bark of the roots of *Solanum dulcamara*.

Fifty minutes thereafter check the bark. On finding the bark dry and brittle, remove the bark from the oven and grind the bark to a powder having a particle size about that of granulated sugar or finer.

With a spatula and on a smooth stone (or other) surface mix three parts of ground bark (BS) with one part of zinc chloride crystals (BZ) until a substantially uniform admixture is obtained in the form of a salve or paste.

EXAMPLE 2

A 39 year old male (MC) was diagnosed by a practicing and qualified physician as having a lesion on the left side of his forehead. Under the observation of the physician a piece of clean white cloth, the size of the lesion, was covered (to the thickness of about that of a dime) with freshly-prepared salve or paste (compounded according to Example 1) to form a plaster. The plaster was placed over the lesion so that the salve was in direct contact with and completely covered the lesion. The plaster was then secured in place with adhesive tape in an air-tight manner, where it was maintained undisturbed and out of contact with moisture for a period of 48 hours.

At the end of that time the tape was removed and the plaster was raised to observe the condition of the lesion, which had a blackish center and appeared white around the edges. The area about the lesion and a considerable surrounding portion of the subject's face was puffed up (swollen).

The plaster was completely removed; the lesion was bathed in luke-warm water with mild soap and then dried. The lesion was then covered with vaseline on which a clean soft white cloth was gently placed and maintained. The washing and drying were repeated twice daily; covering with vaseline was effected after each drying and one additional time each day for seven days, after which a growth (previously referred to as a lesion) fell out. Thereafter the washing and drying were discontinued, but the vaseline treatment (three times each day) was continued until the area was healed.

EXAMPLE 3

The growth removed from MC's forehead in Example 2 was submitted by the physician to a hospital for a pathological report. The report, signed by a qualified pathologist, stated that the "specimen consists of an irregular fragment of ragged, gray-white material measuring 2.0×1.5×0.4 cm. The specimen is serially sectioned and representative sections are submitted. (rwk:cb)"

Microscopic: "Multiple sections show skin with a markedly thin epidermis. In the underlying dermis are nests and sheets of basal cell carcinoma, some of which are surrounded at the periphery by palisading hyperchromatic cells. Marked degeneration and autolysis are noted at the margins of resection. The deep margin is involved with tumor."

Diagnosis: "Skin ellipse, head—basal cell carcinoma. Deep margin involved with tumor; lateral margins indeterminate. (1)"

EXAMPLE 4

Four months after the treatment referred to in Example 2, a biopsy was made of the area of MC's forehead from which the growth had been removed. At that time there was a small unhealed center in the scar, and an ellipseal incision was made widely around the sinus area. This was sent to the same hospital for a pathological report, which was rendered by the same pathologist. The report states that the "specimen consists of an ellipse measuring 1.4×0.6×0.5 cm. The epidermal surface has a slight gray lesion measuring 0.2 cm. in diameter. On cut surface the dermis is gray-white and thickened. Representative sections are submitted (rwk:cb)"

Microscopic: "These sections of skin show an intact elevated epidermis. In the dermis is a nodule consisting of dense collagen. The collagen is arranged in an irregularly intertwining fashion. Around the nodule is a scanty lymphocytic infiltrate. There is no evidence of atypia or malignancy."

Diagnosis: "Nodular subepidermal fibrosis is biopsy from forehead, no malignancy. (1)"

EXAMPLE 5

To treat a melanocytic nevus above and to the right of the chin of a 40 year old white male, a piece of clean white cloth (just slightly larger than the nevus) is covered (to a fairly uniform thickness approximating that of a dime) with freshly-prepared salve or paste compounded according to Example 1, thus forming a plaster. The nevus and surrounding area are dried, and the plaster is placed over the nevus so that the salve or paste is in direct contact with the nevus. The plaster is then secured in place with adhesive tape in a manner designed to exclude external air from the nevus.

For a period of twenty-four hours the adhesive tape and the involved skin area are kept dry and are maintained out of contact of anything having a temperature below about 20°. Thereafter the adhesive is lifted to observe the condition of the nevus, which appears to be circumscribed by a whitish perimeter.

The nevus and immediately surrounding skin is then washed with luke warm water and mild soap and dried before covering it with petroleum jelly. Soft white cloth or gauze is placed over the nevus and maintained in place by contact with the petroleum jelly. Petroleum jelly is kept on the nevus in this manner between washings (and dryings), which are effected twice daily. After eight days the nevus separates from the skin and is effectively removed. Bathing the involved skin and keeping the clean and dried skin in contact with petroleum jelly is continued until the area is healed.

EXAMPLE 6

Following the procedures of Examples 2 and 5 on other persons having similar lesions, but replacing the composition of Example 1 with freshly-prepared salve or paste (having 35, 40, 45, 50 and 55 percent by volume, respectively, of BSO and the remainder BZ) compounded from BSO and BZ, produced corresponding results.

EXAMPLE 7

To treat a skin-colored growth above the lip on the left side of the face of a female patient (RF), BSO was mixed with an equal volume of BZ (3 drops of each). The resulting admixture was placed on a cloth which was applied (with the admixture toward the skin) against the growth so that the growth was completely covered. The cloth was then sealed against the skin with tape and remained in place over the growth for 24 hours. The cloth was removed at the end of that period so that the growth could be examined. There appeared to be a white ring around the edges of the growth, the center of which was a darker, blackish color.

The growth was bathed with mild soap and warm water twice on that day. Following each such washing, vaseline was applied to the growth, which was then covered with a clean cloth. On each of the following two days the growth was bathed three times in the same manner and covered with vaseline and a cloth after each such washing. On the fourth day the vaseline-cloth covering was removed, pressure was applied around the area of the growth, and the growth fell away from the skin. A biopsy of the growth indicated that no carcinoma was present therein.

EXAMPLE 8

To treat a dark growth (similar to a mole) on the inside of the left leg (above the knee) of a twenty-one year old male (DF), BS (from which BSO has been substantially-completely extracted with diethyl ether) was mixed with an equal volume of BZ to make a salve, which was placed on a cloth and applied (in the manner indicated in Example 7) over the growth of DF's left leg. The growth was thus covered, and the covering was sealed against the skin.

The covering with the salve thereon was removed 24 hours later to observe the growth. There was no visible indication of any change in the nature of the growth at that time.

Five days later a clean cloth was saturated with BSO and placed over the same growth before sealing the cloth to surrounding skin with tape. The cover was removed twenty-four hours later to examine the growth, which showed no visible change.

Equal volumes of BSO and BZ were thoroughly mixed and placed on a clean cloth of sufficient size to cover the growth. The cloth was then applied (with the admixture toward the skin) against and completely covering the growth before sealing it securely with tape to the skin. The cloth was removed twenty-four hours later to examine the growth, which was white around the edges. The growth was bathed twice on that day with warm soapy water and then dried before covering it with vaseline on a clean cloth. The washing and vaseline application were repeated three times each day thereafter. When the cloth was removed on the fifth day, a wooden tongue depressor was pressed around the edges of the growth, and the growth fell away from the skin.

EXAMPLE 9

A 51-year old male (AT) had a growth (a basal cell carcinoma) on the right side of his neck under his right ear. The exterior of the growth was larger in size than a half-dollar coin. It had been burnt off on two previous occasions.

A cloth covered with a mixture (equal parts by volume of BSO and BZ) was placed (with the mixture toward the skin) over the growth and sealed against the skin with tape. In view of the large size of the growth, the cloth was allowed to remain for 48 hours before removing it from the growth for examination. At that time the growth was white around the edges.

AT stated that he had some pain during the first eight hours of that 48-hour period. However, it was not necessary for him to take anything for the pain. He further stated that he felt a drawing effect while the admixture was on the growth.

On the day that the admixture was removed from the growth, the growth was bathed twice with warm soapy water and then covered with a cloth with vaseline between the cloth and the growth. The growth was subsequently bathed twice during each of the next four days and similarly covered with vaseline and a white cloth after each such washing. Thereafter, the vaseline-coated cloth was removed, a wooden tongue depressor was pressed around the edges of the growth, and the growth fell away from the skin. This growth was submitted to Nashville Pathology Associates in Nashville, Tennessee, for an evaluation of the growth. The resulting report indicated malignant basal epithelial cells and that normal tissue was present on each side of and beneath the lesion. The diagnosis was basal cell carcinoma of the skin of the neck with marked chronic inflammation. The area in which the growth had been was covered with vaseline to assist healing.

Sixteen days after removal of the growth another biopsy of the area was sent to the same laboratory, which reported that there was no evidence of residual or recurring basal cell carcinoma.

In each of Examples 7, 8 and 9 the skin from which the growth had been removed was treated with vaseline and covered with gauze or a band-aid until completely healed. In the cases reported in Examples 7 and 8 substantially complete healing was effected in from 5 to 6 days.

EXAMPLE 10

Extract 20.51 g of the ground bark referred to in Example 1 with diethyl ether, and evaporate the ether from the resulting extract to obtain 2.2 g (10.7 percent) of dark oil (BSO). Subject the ether extract to thin layer chromatography (TLC). From the plates (marked 1 to 4, respectively, in FIG. 1) the ether extract occurs as a single spot:

Eluting Agent—2 millimeters of acetic acid, 4 milliliters of methanol and 22 milliliters of benzene;
(1) Silica Gel (E. Merck)—$r_f$=0.56
(2) Alumina (Baker)—$r_f$=0.15 (tails to origin)
(3) Kieselguhr—$r_f$=0.99
(4) Polyamide (Baker)—$r_f$=0.86 (in the form of a half moon)

BSO gives a single spot with three different layers, silica gel, kieselguhr and polyamide. The tail produced on alumina suggests a high molecular weight.

Column chromatography on Woelm alumina, activity 1, 90×4 centimeters, produced pure oil (BSO) with hexane as the eluting solvent progressing to pure methylene chloride.

| | | | |
|---|---|---|---|
| Hexane | Fraction 1 | 0.16 g | colorless oil |
| | Fraction 2 | 0.52 g | light yellow, clear oil, barely moves |
| Pure Methylene | Fraction 3 | 0.01 g | |
| Chloride | Fraction 4 | 0.01 g | |

Each fraction had 100 milliliters of eluting solvent. All the dark brown material (as much as 1.5 g) left behind was retained on the first 10 centimeters of the 90-centimeter column. Since the spectra of the crude oil were substantially the same as those of the pure oil, the dark brown material is apparently alike in structure, but greater in molecular weight.

Figure 4:
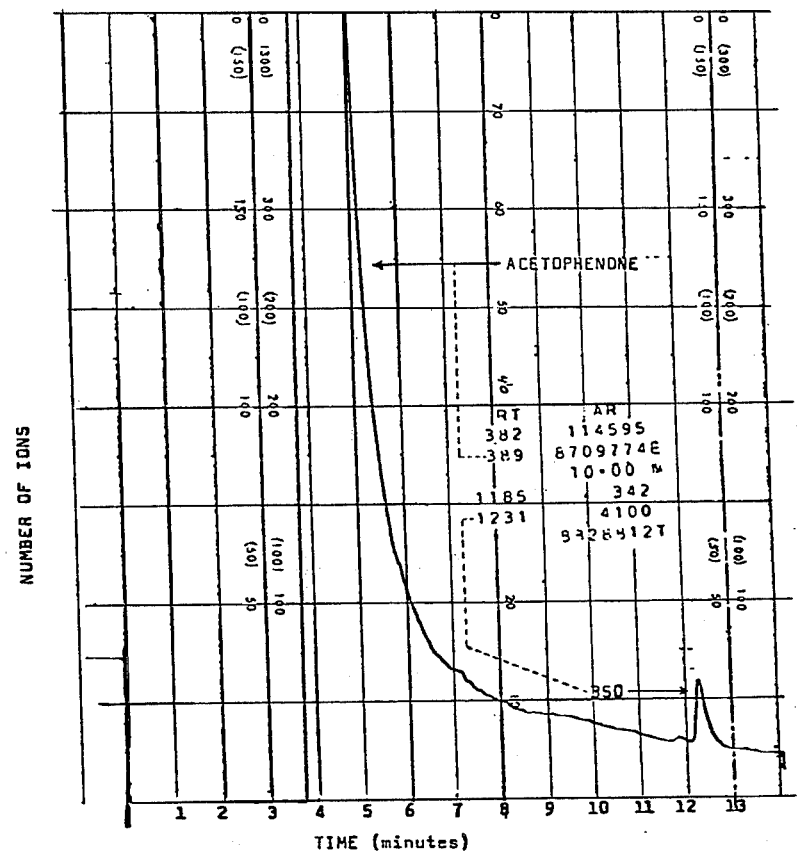
FIG. 4 reflects a comparison of BSO (ether extract) with acetophenone (an internal standard) by gas chromatography.

Gas chromatography (GC) further defines the pure oil extract (BSO) as seen from FIG. 4. The retention time for BSO is 12.31 minutes relative to a retention time of 3.89 minutes for acetophenone (an internal standard). These times are computer times.

The other relevant parameters are:
Machine: Shimadzu, Mini-2
Column: 40 meter capillary, glass
Coating: OV-101
Flow-rate of hexane: 88 milliliters/minute, 100 to 1 splitter
Column Temperature: 200° C.
Injector Temperature: 210° C.
Attenuation: 64
Range: 1

The long retention time is indicative of a molecular weight somewhere near 430. The structure is aliphatic or in the form of one or more rings. A structure with six isoprene units (four hydrogen atoms of which are replaced by two keto oxygen atoms) and in which each such unit

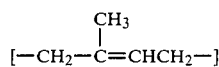

is optionally in the form of a 6-membered ring is projected.

Elemental Analysis of the pure oil extract (BSO) revealed 81.17 percent carbon, 11.42 percent hydrogen and 7.41 percent (by difference) oxygen. This corresponds to the formula of a sesquiterpene: $C_{15}H_{25}O$ (or a multiple thereof), having one carbonyl, one C=C double bond and one ring closure or a similar combination, e.g. one carbonyl, two C=C double bonds and no ring closure.

Figures 2, 3:
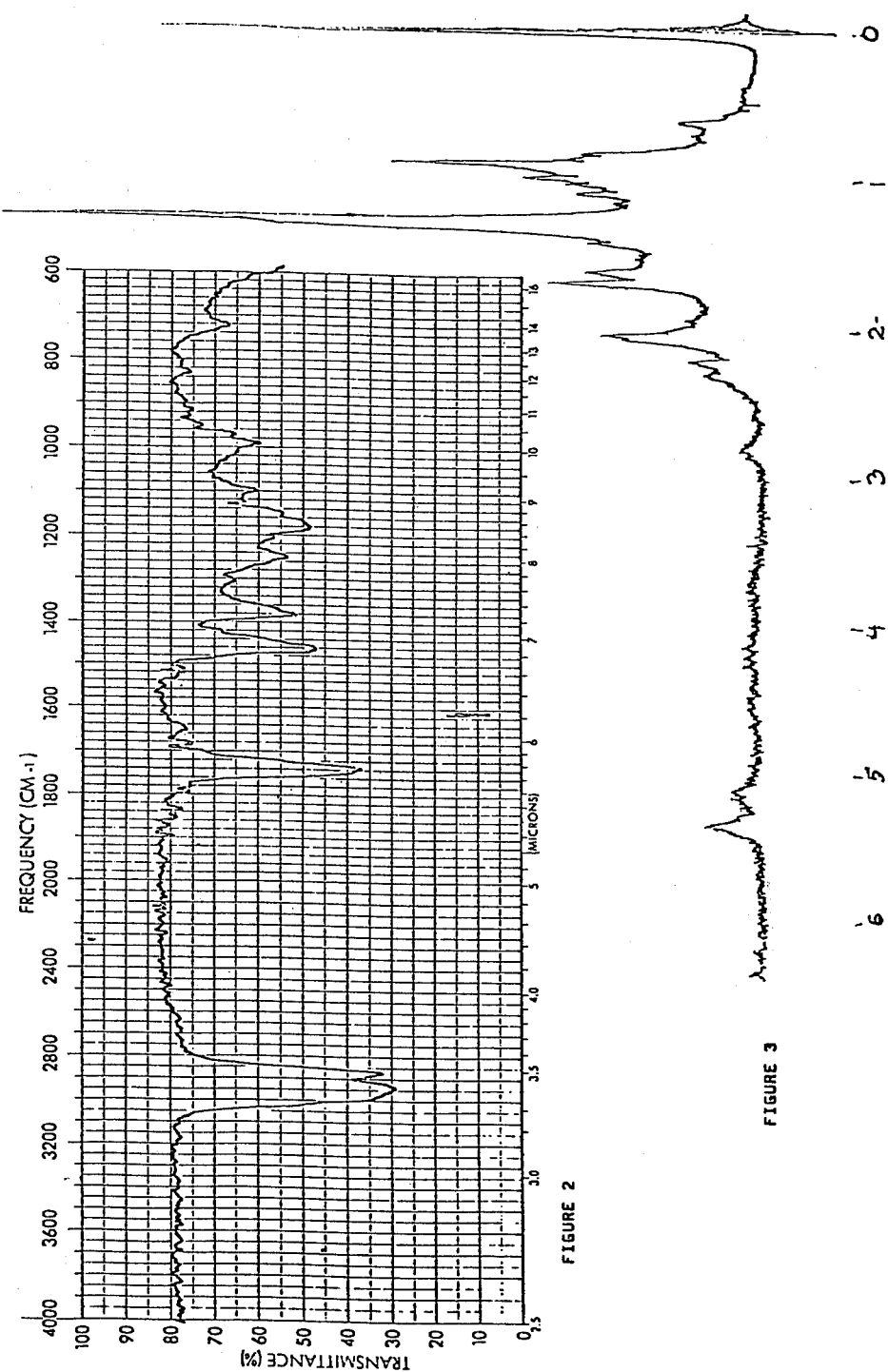
FIG. 2 is the infrared spectrum for BSO (ether extract).
FIG. 3 is the nuclear magnetic resonance spectrum for BSO (ether extract).

The infrared (IR) spectrum for the pure oil extract (BSO) is shown in FIG. 2. This confirms the presence of a carbonyl group (1750 cm$^{-1}$) and the absence of a hydroxyl group.

The nuclear magnetic resonance (NMR) spectrum (run in deuterated chloroform) for the pure oil (BSO) is shown in FIG. 3. The signal at 5.3 parts per million (ppm) indicates a (C=C) double bond. The long sharp peak at 1.3 ppm is indicative of at least two methyl groups. The peaks at 2 ppm indicate hydrogen on a carbon next to carbonyl.

The noted elemental analysis of BSO (which lacks nitrogen) confirms the terpene structure and the approximate empirical formula of $C_{15}H_{25}O$ or a multiple thereof. Calculated analyses for possible empirical formulae are:

| Molecular | | Calculated (%) | | |
| --- | --- | --- | --- | --- |
| Weight | Formula | C | H | O |
| 221 | $C_{15}H_{25}O$ | 81.39 | 11.38 | 7.23 |
| 430 | $C_{29}H_{49}O_2$ | 81.06 | 11.49 | 7.45 |
| 442 | $C_{30}H_{49}O_2$ | 81.57 | 11.18 | 7.24 |
| 443 | $C_{30}H_{50}O_2$ | 81.39 | 11.38 | 7.23 |
| 444 | $C_{30}H_{51}O_2$ | 81.20 | 11.58 | 7.21 |

The calculated formula for $C_{29}H_{49}O_2$ most closely approximates the C-H-O values ($C_{14.6}H_{24.6}O_{1.0}$) found.

BSO is also extractable from roots and vines of *Solanum dulcamara*. The reference to the terpene structure covers all isoprene structures

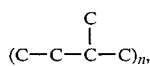

whether n is 1, 2, 3, 4, 5 or greater or whether carbon bonds are branched or cyclic. In such structures wherein n is more than 1, it is not unusual for one or two carbons to be lost by metabolic oxidation, thus permitting the possibility of $C_{29}H_{49}O_2$ as the actual empirical formula.

The invention and its advantages are readily understood from the foregoing description. Although it is apparent that various changes may be made in the process and compositions without departing from the spirit or scope of the invention or sacrificing its material advantages, the compositions requires a combination of the two ingredients indicated to be essential. Neither ingredient alone will produce the results obtained with the combination. The hereinbefore described processes and products are merely illustrative or preferred embodiments of the invention.

What is claimed is:

1. The diethyl ether-soluble compound, which is an oil having the following properties:
   (1) approximate empirical formula—$C_{15}H_{25}O$ or a multiple thereof;
   (2) thin layer chromatograph (TLC)—single spots (eluting solvent—22 parts by volume of benzene, 2 parts by volume of acetic, 4 parts by volume of methanol)
     $r_f$=0.56 on silica gel (Merck F-254)
     $r_f$=0.15 (tails to origin) on alumina (Baker)
     $r_f$=0.99 on kieselguhr
     $r_f$=0.86 (in half-moon form) on polyamide (Baker);
   (3) infrared (IR) absorption spectrum as set forth in FIG. 2;
   (4) nuclear magnetic resonance (NMR) as set forth in FIG. 3;
   (5) gas chromatography (GC)
     Retention Time—12.3 minutes (as compared with 3.9 minutes for acetophenone, an internal standard)
     Machine: Shimadzu, Mini-2
     Column: 40 meter capillary
     Coating: OV-101
     Column Temperature: 200° C.
     Injector Temperature: 210° C.
     Attenuation: 64
     Range: 1.

2. A pharmaceutically-acceptable composition for treating skin topically and consisting essentially of an admixture of (a) zinc chloride with (b) the compound of claim 1, the weight ratio of (a):(b) being within the range of from 1:20 to 20:1.

3. A composition according to claim 2 wherein the amount of (b) is from 35 to 55 percent by volume that of the sum of (a) and (b).

4. A pharmacologically-acceptable topically-applicable composition suitable for removing a skin lesion, having a consistency from that of a thin paste to that of a dough-like salve and consisting essentially of an effective admixture of (a) zinc chloride with (b) the compound of claim 1.

5. A composition according to claim 4 which is substantially free from water.

6. A process for treating a skin lesion on a patient which comprises topically applying an effective amount of a composition according to claim 4, to the lesion.

7. A process according to claim 6 which comprises removing a mole.

8. A process according to claim 6 which comprises removing a wart.

9. A process according to claim 6 wherein the medicament composition is a substantially uniform admixture of zinc chloride in crystal form with (b).

* * * * *